(12) United States Patent
Elsheikh et al.

(10) Patent No.: US 9,809,515 B2
(45) Date of Patent: *Nov. 7, 2017

(54) DEHYDROFLUORINATION OF PENTAFLUOROALKANES TO FORM TETRAFLUOROOLEFINS

(71) Applicant: ARKEMA INC., King of Prussia, PA (US)

(72) Inventors: Maher Y. Elsheikh, Wayne, PA (US); Philippe Bonnet, Lyons (FR); Olga C. N. Keeley, San Francisco, CA (US); Benjamin Bin Chen, Wayne, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/279,680

(22) Filed: Sep. 29, 2016

(65) Prior Publication Data
US 2017/0022128 A1    Jan. 26, 2017

Related U.S. Application Data

(63) Continuation of application No. 13/695,807, filed as application No. PCT/US2011/034890 on May 3, 2011, now Pat. No. 9,492,816.
(Continued)

(51) Int. Cl.
*C07C 17/25*    (2006.01)
*C07C 21/18*    (2006.01)
(Continued)

(52) U.S. Cl.
CPC ............. *C07C 17/25* (2013.01); *B01J 21/18* (2013.01); *B01J 23/26* (2013.01); *B01J 27/132* (2013.01);
(Continued)

(58) Field of Classification Search
CPC .................................................. C07C 17/25
See application file for complete search history.

(56) References Cited

U.S. PATENT DOCUMENTS 6,124,510 A    9/2000  Elsheikh et al. ............. 570/156
7,476,771 B2   1/2009  Miller et al.
(Continued)

FOREIGN PATENT DOCUMENTS

FR    WO 2009118630 A1 * 10/2009 ............ B01J 23/866
WO    WO 2008040969 A2    4/2008
WO    WO 2009003157 A1    12/2008

OTHER PUBLICATIONS

WO 2009118630 A1, Oct. 1, 2009, pp. 1-16; English translation.*
(Continued)

*Primary Examiner* — Medhanit Bahta
(74) *Attorney, Agent, or Firm* — Steven D. Boyd

(57) ABSTRACT

A method for producing a tetrafluoroolefin, such as 2,3,3,3-tetrafluoropropene (HFO-1234yf), comprises dehydrofluorinating a pentafluoroalkane in a gas phase in the presence of a catalyst comprising chromium oxyfluoride. In a preferred embodiment, 2,3,3,3-tetrafluoropropene (HFO-1234yf) is produced by forming a catalyst comprising chromium oxyfluoride by calcining $CrF_3 \cdot xH_2O$, where x is 1-10, in the presence of a flowing gas comprising nitrogen to form a calcined chromium oxyfluoride, and dehydrofluorinating 1,1,1,2,2-pentafluoropropane (HFC-245cb) in a gas phase in the presence of the catalyst to form the 2,3,3,3-tetrafluoropropene (HFO-1234yf).

14 Claims, 1 Drawing Sheet

Related U.S. Application Data

(60) Provisional application No. 61/324,056, filed on May 3, 2010.

(51) Int. Cl.
*B01J 23/26* (2006.01)
*B01J 27/132* (2006.01)
*B01J 37/08* (2006.01)
*B01J 21/18* (2006.01)
*B01J 37/00* (2006.01)
*B01J 37/14* (2006.01)

(52) U.S. Cl.
CPC ....... *B01J 37/0018* (2013.01); *B01J 37/0072* (2013.01); *B01J 37/08* (2013.01); *B01J 37/14* (2013.01)

(56) References Cited

U.S. PATENT DOCUMENTS

| | | |
|---|---|---|
| 2009/0306438 A1 | 12/2009 | Sievert et al. ............... 570/157 |
| 2010/0004492 A1 | 1/2010 | Nappa et al. |
| 2011/0015452 A1 | 1/2011 | Devic et al. |
| 2011/0124930 A1 | 5/2011 | Smith et al. |

OTHER PUBLICATIONS

Chung, Y., et al., Enhanced Catalytic Activity of Air-Calcined Fluorination Catalyst, Journal of Catalysis, 175, 1998, pp. 220-225.
Chung, Y. S. et al. Journal of Catalysis 1998, 175, 220-225.

\* cited by examiner

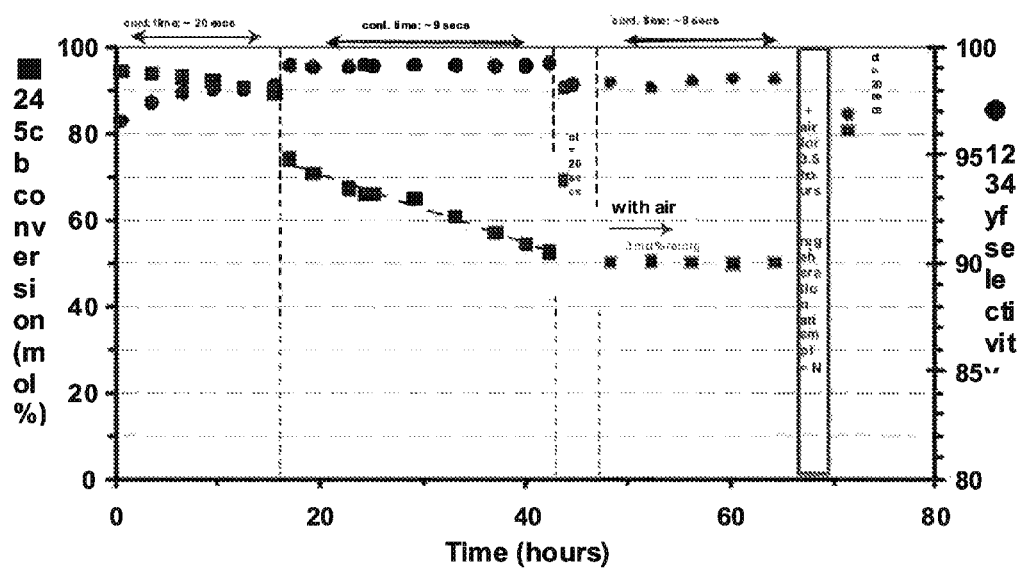

DEHYDROFLUORINATION OF PENTAFLUOROALKANES TO FORM TETRAFLUOROOLEFINS

This application is continuation of U.S. patent application Ser. No. 13/695,807, filed Nov. 2, 2012, which is the United States national phase of and claims priority to International Application serial number PCT/US11/034890 filed May 3, 2011 which designated the United States, which claims priority to U.S. provisional application Ser. No. 61/324,056 filed May 3, 2010, all of which are incorporated herein by references.

FIELD OF THE INVENTION

The invention relates to a method of making tetrafluoroolefins, such as 2,3,3,3-tetrafluoropropene (HFO-1234yf), from pentafluoroalkanes.

BACKGROUND OF THE INVENTION

Chlorine-containing compounds such as chlorofluorocarbons (CFCs) are ozone depleting substances. Many of the hydrofluorocarbons (HFCs), used to replace CFCs, have been found to contribute to global warming. Therefore, compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids, have been investigated. Fluorinated olefins, especially those containing one or more hydrogens in the molecule (referred to herein as hydrofluoroolefins (HFOs)) are being considered for use in some of these applications, such as in refrigeration as well as in processes to make fluoropolymers. In particular, HFO-1234yf may be useful as a refrigerant composition and has a lower potential to contribute to global warming than refrigerant compositions, such as HFC-134a.

The manufacture of tetrafluoroolefins, such as HFO-1234yf, has been shown to suffer from a number of drawbacks, such as, custom manufactured catalysts, expensive manufacturing costs, multiple-step processes, high pressure hydrogen fluoride (HF) activation, etc. Also, the catalysts used in the manufacture of tetrafluoroolefins, such as HFO-1234yf, have suffered from fast deactivation and/or were not suited for air regeneration, which would lead to catalysts being regularly discarded after use.

SUMMARY OF THE INVENTION

The methods according to the present invention provide practical industrial methods for manufacturing tetrafluoroolefins, and particularly, HFO-1234yf. The catalysts used in the process were found to be active, selective dehydrofluorinating catalysts, which may be obtained from readily available commercial compounds. Accordingly, tetrafluoroolefins, such as HFO-1234yf, may be obtained from a practical, inexpensive process. The catalysts and methods of the present invention provided reactions with relatively high conversion and relatively high selectivity. In addition, depending on the selection of the catalysts, HF activation may not be required. Also, the catalysts may be run for extended periods of time without the need for frequent catalyst regeneration, and the catalysts can be easily regenerated, for example, using air.

According to an embodiment of the present invention, a method for producing tetrafluoroolefins, such as 2,3,3,3-tetrafluoropropene (HFO-1234yf), comprises dehydrofluorinating a pentafluoroalkane in a gas phase in the presence of a catalyst comprising chromium oxyfluoride.

According to another embodiment of the present invention, a method for producing a tetrafluoroolefin, such as 2,3,3,3-tetrafluoropropene (HFO-1234yf), comprises contacting a pentafluoroalkane in a gas phase with a catalyst comprising chromium oxyfluoride under conditions effective to dehydrofluorinate the pentafluoroalkane.

According to another embodiment of the present invention, a method for producing 2,3,3,3-tetrafluoropropene (HFO-1234yf) comprises forming a chromium oxyfluoride catalyst, and dehydrofluorinating 1,1,1,2,2-pentafluoropropane (HFC-245cb) in a gas phase in the presence of the catalyst to form 2,3,3,3-tetrafluoropropene (HFO-1234yf). The catalyst may be formed by calcining $CrF_3 \cdot xH_2O$, where x is 1-10, in the presence of a flowing gas comprising nitrogen to form a calcined chromium oxyfluoride or by activating $Cr_2O_3$ with hydrogen fluoride to form an activated chromium oxyfluoride.

BRIEF DESCRIPTION OF THE DRAWINGS

The invention may be understood from the following detailed description when read in connection with the accompanying drawing. Included in the drawing is the following FIGURE:

The FIGURE is a graph illustrating the conversion of HFC-245cb in mol % and the selectivity to HFO-1234yf over time.

DETAILED DESCRIPTION OF THE INVENTION

Aspects of the present invention include methods for producing tetrafluoroolefins, such as 2,3,3,3-tetrafluoropropene (HFO-1234yf), and the catalysts used during the production methods thereof. The methods of the present invention convert pentafluoroalkane compounds to the corresponding tetrafluoroolefin.

As used herein, HFO designates hydrofluoroolefins and HFC designates hydrofluorocarbons. Each species may be discussed interchangeably with respect to its chemical formula, chemical name, or abbreviated common name. For example, 2,3,3,3-tetrafluoropropene may be designated as $CH_2=CFCF_3$, HFO-1234yf, or 1234yf. As used herein, unless specified otherwise, the values of the constituents or components are expressed in either weight or molar percent of each ingredient.

According to one embodiment of the present invention, a method for producing a tetrafluoroolefin, such as 2,3,3,3-tetrafluoropropene (HFO-1234yf), comprises dehydrofluorinating a pentafluoroalkane in a gas phase in the presence of a catalyst comprising chromium oxyfluoride.

A tetrafluoroolefin is the desired reaction product obtained. The tetrafluoroolefin obtained depends upon the pentafluoroalkane chosen. In an exemplary embodiment, the tetrafluoroolefin is a tetrafluoropropene, which is obtained from a pentafluoropropane, such as 245cb or 245eb. 2,3,3,3-Tetrafluoropropene, or HFO-1234yf, is a fluorinated hydrocarbon with the formula $CH_2=CFCF_3$. HFO-1234yf is a non-ozone-depleting fluorocarbon replacement with a lower global warming potential (e.g., <150) and may be used as a potential refrigerant for the car industry. In particular, HFO-1234yf may be suitable as a refrigerant for mobile air conditioning (MAC) applications. It has been found that the HFO-1234yf may be efficiently produced by contacting a pentafluoroalkane in a gas phase with a catalyst comprising chromium oxyfluoride under conditions effective to dehydrofluorinate the pentafluoroalkane.

The dehydrofluorination may be carried out using a feed stock, such as a hydrofluorocarbon. The hydrofluorocarbons may be acyclic, linear, or branched compounds containing hydrogen and fluorine located on adjacent carbon atoms. In an exemplary embodiment, the hydrofluorocarbon is a pentafluoroalkane (i.e., alkanes comprising five fluorine groups). Any suitable pentafluoroalkane may be selected, including, but not limited to, 1,1,1,2,2-pentafluoropropane (HFC-245cb); 1,1,1,2,3-pentafluoropropane (HFC-245eb); 1,1,1,3,3-pentafluorobutane (HFC-365mfc); 1,1,1,2,2-pentafluoroethane (HFC-125); 1,1,1,3,3-pentafluoropropane (HFC-245fa); hexafluoropropanes, such as 1,1,1,2,3,3-hexafluoropropane (HFC-236ea) and 1,1,1,3,3,3-hexafluoropropane (HFC-236fa); and mixtures thereof.

In an exemplary embodiment, the pentafluoroalkane is selected from the group consisting of 1,1,1,2,2-pentafluoropropane (HFC-245cb); 1,1,1,2,3-pentafluoropropane (HFC-245eb); 1,1,1,3,3-pentafluorobutane (HFC-365mfc); 1,1,1,2,2-pentafluoroethane (HFC-125), and mixtures thereof. In a preferred embodiment, the pentafluoroalkane is 1,1,1,2,2-pentafluoropropane (HFC-245cb) and/or 1,1,1,2,3-pentafluoropropane (HFC-245eb).

During dehydrofluorination, it is believed that the following reactions are representative of the dehydrofluorination which occurs in preferred operations:

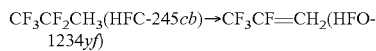

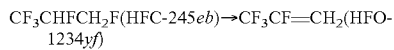

The dehydrofluorination of a pentafluoroalkane may be carried out in the vapor phase. The gas phase reaction may be conducted, for example, by introducing a gaseous form of the pentafluoroalkane, which may be at room temperature or preheated using a pre-heater.

In an exemplary embodiment, a pure pentafluoroalkane or mixture thereof can be used as a feedstock to be dehydrofluorinated, e.g., the reactant feed consists of a pure pentafluoroalkane, such as HFC-245cb, HFC-245eb, or mixture thereof. In one embodiment, a blend of HFC-245cb and HFC-245eb is used as the feed stock which is dehydrofluorinated.

Other gases may also be co-fed with the pentafluoroalkane, such as, air, pure oxygen or mixtures of oxygen and nitrogen, e.g., to mimic an air composition. For instance, it was found that the catalyst activity can be maintained for an extended period of time by co-feeding low levels of oxygen with the pentafluoroalkane. For example, oxygen may be present in the gas phase in an amount effective to provide an oxygen to pentafluoroalkane molar ratio of about 0.1-10%. More preferably, about 0.1-2 molar % low level of oxygen may be co-fed with the pentafluoroalkane. In an exemplary embodiment, the co-feed is an oxygen-containing gas, such as air.

Vapor phase dehydrofluorination of a pentafluoroalkane is suitably carried out using a dehydrofluorination catalyst. The catalyst comprises chromium, oxygen, and fluoride. In a preferred embodiment, the catalyst is chromium oxyfluoride, of the formula CrOF, in the presence of co-catalyst, selected from Zn, Co, Ni, Mn and/or Mg, supported or unsupported.

The present invention involves, in one aspect, methods of making the chromium oxyfluoride catalyst. The catalytic gas phase dehydrofluorination of a pentafluoroalkane intermediate, such as 245cb, may occur by using a catalyst prepared from a commercial fluorided chromium compound as the catalyst precursor. Any suitable fluorided chromium compound may be selected, such as $CrF_3 \cdot xH_2O$, $Cr/Ni/AlF_3$, fluorided $Cr_2O_3$, etc. The chromium fluoride compound may be anhydrous or hydrated, but is preferably hydrated. The fluorided chromium compound, such as $CrF_3 \cdot xH_2O$, is first calcined. The calcination may occur under any suitable conditions. For example, during the calcination, the chromium fluoride may be heated to a temperature between about 200-1000° C., preferably between about 400-500° C. The chromium fluoride may be heated up in a stream or atmosphere of at least one inert gas, such as nitrogen, helium, or argon. In an exemplary embodiment, the chromium fluoride is heated in a stream of nitrogen to calcine the catalyst precursor. It is also possible to calcine the hydrated chromium fluoride using an active gas (e.g., a gas capable of reacting, such as air). The inert gas or active gas may be pre-heated or the reactor may be heated once the catalyst precursor and the inert gas are contained therein. A contact time between the heated inert gas/or active gas and the catalyst precursor may be about 10-200 seconds, preferably 10-100 seconds, more preferably about 20-50 seconds. The operating pressure is not particularly critical and may be between atmospheric and lower vacuum e.g., 1-10 mmHg. It may be preferred to avoid high pressure calcinations, however.

In an exemplary embodiment, the catalyst is formed by calcining $CrF_3 \cdot xH_2O$, where x is 1-10, or more preferably x is 3-5, to form a calcined chromium oxyfluoride. In a preferred embodiment, the catalyst is chromium (III) fluoride tetrahydrate where x equals 4 (i.e., $CrF_3 \cdot 4H_2O$).

Without wishing to be bound to a particular theory, it is believed that the calcination of the chromium fluoride using an inert gas, such as nitrogen, or active gas, such as air, proceeds by a dehydration step and a hydrolysis step to form the chromium oxyfluoride catalyst. The following reaction schemes may be representative of the (1) dehydration and (2) hydrolysis steps:

 (1)

 (2)

Any by-products, including the hydrogen fluoride and/or water generated, may be separated from the chromium oxyfluoride if desired using any suitable means known in the art. The calcined chromium oxyfluoride may then be used as the catalyst in the dehydrofluorination reaction.

Unlike the prior art, however, the calcined chromium oxyfluoride may be formed without requiring a high pressure HF activation. See, for example, WO2009/003084 in which the catalyst requires an additional high pressure HF activation. Thus, the dehydrofluorinating catalyst or catalyst precursor utilized in the present invention requires no hydrogen fluoride activation and, in an exemplary embodiment, the catalyst is not activated with hydrogen fluoride. Therefore, the calcined chromium oxyfluoride may be directly used in the dehydrofluorination or may undergo further processing, such as pelletizing. The calcined chromium oxyfluoride provides good selectivity and conversion to 1234yf, in a simple, single step process.

In another embodiment, the catalyst is formed by activating a chromium-containing compound, such as $Cr_2O_3$, with hydrogen fluoride to form an activated chromium oxyfluoride. The activation may be represented by the following reaction:

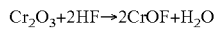

Thus, the catalyst or its precursor may undergo a hydrogen fluoride activation based on the starting catalyst material selected. A catalyst activated with hydrogen fluoride has also been found to exhibit good selectivity and good conversion to 1234yf.

The catalyst may be unsupported or supported. When supported, the catalyst may be supported using one or more suitable supports, such as activated carbon, graphite, chromia, alumina, zirconia, titania, magnesia, or their corresponding HF-activated compounds, such as fluorinated graphite, fluorinated chromia, fluorinated alumina, etc. In an exemplary embodiment, the catalyst comprises at least one support selected from the group consisting of alumina, fluorinated alumina, chromia, fluorinated chromia, activated carbon, HF-activated carbon, and mixtures thereof. In a preferred embodiment, $CrF_3$, or preferably CrOF, is supported on alumina. When the catalyst is supported, it is suitable that the amount of chromium carried thereon is about 1-20 total wt %, preferably about 5-10 total wt %. The catalyst does not require a co-catalyst, but a co-catalyst, such as nickel, cobalt, manganese, and zinc, may be included therewith. In one embodiment, the catalyst is obtained by calcination of precursor mixture comprising chromium, nickel, and $AlF_3$. In an exemplary embodiment, the only catalytically active substance in the catalyst is chromium oxyfluoride (i.e., the catalyst does not comprise a co-catalyst).

The physical shape of the catalyst is not particularly limited. In one embodiment, the catalyst is in the shape of pellets or granules. The catalyst may be combined with other ingredients, such as graphite, which may function as a bonding agent for making stronger pellets and/or to operate under pressure without attrition. Additionally, for supported catalysts, the supports may also be in the form of granules or pellets, or the like. In an exemplary embodiment, the catalyst is pelletized and the pellet size is between about 1/16" to 1/4", depending on the reactor diameter. It is contemplated that the amount of catalyst used will vary depending on the particular parameters present during the reaction, which could be readily ascertainable by one of ordinary skill in the art. Other ingredients may also be added to the catalyst for use in the reactor, such as a bonding agent. For example, about 1-5 weight % of a bonding agent, such as graphite or alumina, may be used.

By using the methods described herein to form the chromium oxyfluoride, a simple single step process may be used to provide an inexpensive dehydrofluorination catalyst. The dehydrofluorination catalysts described herein, unlike the prior art, may dehydrofluorinate for a significant period of time with minimal or no catalyst deactivations or deteriorations. For example, U.S. Publication No. 2007/0197841 describes an activated carbon catalyst, which may deactivate quickly due to carbon deposition, and in this particular case, the catalyst will not be regenerated because of the presence of activated carbon as a support. Thus, the catalysts of the present invention can run for an extended period of time without the need for catalyst regeneration. Also, if needed, the catalyst may be regenerated. For example, the deactivated catalyst may be regenerated by using hot air for an effective contact time. An effective contact time may be between 1-100 seconds under operating temperatures at about 300-400° C. The duration of the catalyst regeneration is not particular limited, but may occur for about 5-18 hours or until all of the carbon deposits have been released, for example, as carbon dioxide.

The gas phase reaction may be conducted in any suitable reaction vessel or reactor. The vessel or reactor may be of any suitable type, shape, and size. For example, the reactor may be a fixed or fluid catalyst bed reactor, a tubular reactor, etc. Because dehydrofluorination is an endothermic reaction, the reactor should be equipped to apply heat to the reaction zone as appropriate. Also, it is known to one of ordinary skill in the art that hydrogen fluoride is corrosive, and the reactor should be constructed accordingly when HF may be present. In one embodiment of the present invention, pelletized catalyst may be loaded into a fixed bed reactor, mounted inside a three-zone furnace, which may be heated up electrically. The reaction may be carried out batch wise, continuous, or any combination of these. The reaction may be performed using a wide variety of process parameters and process conditions readily ascertainable to one of ordinary skill in the art based on the teachings provided herein.

The catalytic dehydrofluorination may be carried out in the presence of an inert gas, such as nitrogen, helium or argon. Nitrogen is a preferred inert gas. The process may also be carried out in the presence of an oxygen containing gas, such as air, as an oxidizer to oxidize any carbonous deposit to $CO_2$ gas. The latter condition is preferable over the use of inert gas, because it can extend the lifetime of the catalyst.

The operating conditions and residence time of the reactants in the reactor should be sufficient for the reaction of the pentafluoroalkane to take place with an acceptable yield, which may be determined as a function of the operating conditions adopted. The catalytic dehydrofluorination may be suitably conducted at a temperature in the range of from about 200° C. to about 800° C., and, in another embodiment, from about 300° C. to about 600° C., and more preferably about 300° C. to 450° C. The contact time may be from typically from about 1 to about 450 seconds, and, in another embodiment, from about 10 to about 200 seconds. In one example, a feed comprising at least one pentafluoroalkane, such as HFC-245cb, may be fed using a mass flow meter controller at a feed rate which corresponds to about 10-100 second contact time.

The reaction pressure can be subatmospheric, atmospheric, or superatmospheric. Generally, near atmospheric pressures are preferred. In an exemplary embodiment, the operating pressure varied between atmosphere to about 1-10 bars, preferably and for practical purposes at about atmospheric pressure.

The hydrofluorocarbons are dehydrofluorinated to form the hydrofluoroolefin, and other co-products may also be formed, such as hydrogen fluoride. In certain circumstances, an azeotropic mixture may result. As recognized in the art, an azeotrope or a near-azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling. For example, an azeotrope may form when HF is present along with unreacted hydrofluoropropane and the reaction product.

The azeotrope containing the tetrafluoroolefin, such as HFO-1234yf, may be separated and/or the other reactant products or unreacted feedstock may be separated from the tetrafluoroolefin using suitable techniques known to those skilled in the art. For instance, the separation may be accomplished by swing distillation, solvent extraction, membrane separation, scrubbing, adsorption, and the like. For example, the generated HF in the process may be separated from organic product or unreacted feedstock by adsorption using solid alkali metals, such as KF or NaF. Other means of acid separation, such as water or aqueous alkaline scrubbing can be used, followed by organic drying using a solid drier, such as anhydrous $CaSO_4$ or other drying agents known in the art. Any other suitable means of separation, such as membrane can also be used to separate HF from the organic constituents.

Accordingly, in one embodiment, a process comprises contacting at least one pentafluoropropane with a chromium oxyfluoride catalyst in a reactor to obtain a product mixture comprising a tetrafluoroolefin, such as 2,3,3,3-tetrafluoropropene (HFO-1234yf), and recovering said tetrafluoroolefin from said product mixture, for example, by using separation techniques. Optionally, the tetrafluoroolefin may be purified according to known methods. Additionally, unreacted feedstock and/or separated organic impurities may be recycled back into the reactor to reuse it as the starting raw material of the present invention.

According to another embodiment, a method for producing 2,3,3,3-tetrafluoropropene (HFO-1234yf) comprises forming a catalyst comprising chromium oxyfluoride; and dehydrofluorinating 1,1,1,2,2-pentafluoropropane (HFC-245cb) in a gas phase in the presence of the catalyst to form 2,3,3,3-tetrafluoropropene (HFO-1234yf). The catalyst may be formed by calcining $CrF_3.xH_2O$, where x is 1-10, preferably, in the presence of a flowing gas comprising nitrogen or air at a temperature between about 200-1000° C. for a contact time of about 10-100 seconds, to form a calcined chromium oxyfluoride. Alternatively, the catalyst may formed by activating $Cr_2O_3$ with hydrogen fluoride to form an activated chromium oxyfluoride. As discussed above the catalyst may be in any suitable form, but is preferably pelletized as appropriate for the reactor, for example, to a size on the order of about 1/16" to 1/4".

The methods and catalysts described herein produce a tetrafluoroolefin, such as 1234yf, with high selectivity and high conversion. Unlike the prior art, the methods of the present invention provide for improved production of tetrafluoroolefins because the catalysts may run for extended periods of time with low to minimal deactivation. Also, the catalyst may be reactivated easily, for example, with air. The chromium oxyfluoride catalysts are also produced easily and cheaply using commercially available compounds. In addition, some of the catalysts do not require HF activation. Therefore, the methods and catalyst used therein according to the invention have good performance and characteristics especially for the production of the tetrafluoroolefin, 1234yf.

EXAMPLES

Prophetic Example 1—Preparation of CrOF Powder Catalyst A 100 grams (0.55 moles) of the catalyst precursor $CrF_3.4H_2O$ may be placed in a fixed bed reactor. The catalyst may be supported inside the reactor using a screen. The catalyst precursor may be heated up electrically using a three zone furnace, at a feed rate of about 10 cc/min, with a continuous feed of nitrogen stream at 20 cc/min. The reactor temperature may be raised and maintained at 400° C. for approximately 18 hours (e.g., until all of the water is released). The reactor may then be unloaded and the dry catalyst may be recovered (catalyst A). The chromium fluorine contents may be about 60 wt. % Cr and 0.22 wt. % F.

Prophetic Example 2—Preparation of the Pelletized 3/16" Catalyst B 20 grams of catalyst A may be intimately mixed with one gram of graphite using a mortar and pestle. The fine powder mixture may be placed inside a 3/16" pelletizer using a hydraulic pressure operated at about 10,000 psi. The resulted pelletized catalyst is catalyst B.

Prophetic Examples 3 and 4—Possible Conditions and Outcomes

Table 1 shows theoretical examples 3 and 4 based on catalyst A and catalyst B described above. It is theorized that when catalyst A (powder) and catalyst B (pelletized) are each used for the dehydrofluorination of HFC-245cb, a high selectivity for HFO-1234yf will result. It is also contemplated that a high conversion will also result.

TABLE 1

|  | Example 3 (catalyst A) | Example 4 (catalyst B) |
| --- | --- | --- |
| Catalyst volume (CC) | 20 | 20 |
| Temperature (° C.) | 350 | 350 |
| Pressure (bar) | 1 | 1 |
| Contact time (sec) | 110 | 10 |
| $O_2$/245cb (MR) | 1 | 1 |
| % conversion | 95 | 85 |
| % selectivity for 1234yf | 98 | 98 |
| % selectivity for 1,1,1-trifluoropropyne | 1 | 1 |
| % selectivity for 1234ze | 1 | 1 |

Working Example 5—Dehydrofluorination of 245eb to 1234yf

In this example, the catalyst was activated using hydrogen fluoride. To a Hastelloy C fixed bed reactor, 3/4" by 16", interconnected to anhydrous HF gas and organic HFC-245eb, was placed 23 cc of $Cr_2O_3$ catalyst precursor (described in Table 2 below as bulk Cr1810 catalyst). After drying the catalyst precursor, it was HF activated under pressure, according to a known process in the art (e.g., explained in U.S. Pat. No. 7,485,598, herein incorporated by reference). Subsequently, HFC-245eb was fed over the catalyst bed according to the following processing conditions: 377° C., 1 atm, ct=8.8 secs, molar ratio $N_2$/245eb=1.4. After scrubbing the acid generated and drying the organic product, the product was analyzed using gas chromatography on line as described in U.S. Pat. No. 7,485,598. A summary of the results, together with other catalysts evaluated under similar conditions, is shown in Table 2 below.

TABLE 2

| catalysts tested | conversion (mol %) | selectivity (mol %) 1234yf | 1234ze | 245cb | 236a | CO + CO$_2$ | total |
|---|---|---|---|---|---|---|---|
| AlF$_3$ | 33.54 | 68.81 | 19.78 | 3.79 | 7.58 | 0.00 | 99.96 |
| 20 wt % Cr/Al2O$_3$ | 3.41 | 68.53 | 28.46 | 2.88 | 0.00 | 0.00 | 99.86 |
| 6 wt % Ni/AlF$_3$ | 97.18 | 78.73 | 15.38 | 3.66 | 1.97 | 0.24 | 99.98 |
| 6 wt % Ni-6 wt % Cr/AlF$_3$ | 99.58 | 83.28 | 9.53 | 4.85 | 2.35 | 0.00 | 100.00 |
| 8.5 wt % Cr/C | 100.00 | 79.65 | 14.23 | 3.31 | 2.80 | 0.00 | 99.99 |
| bulk Cr (Cr1810) | 99.71 | 80.69 | 10.02 | 6.81 | 1.96 | 0.44 | 99.92 |
| 2.5 wt % Ni doped bulk Cr | 100.00 | 76.84 | 16.43 | 3.86 | 1.40 | 1.32 | 99.86 |
| 5 wt % Ni doped bulk Cr | 100.00 | 77.64 | 16.08 | 3.71 | 1.25 | 1.19 | 99.88 |
| 5% Ni doped bulk Cr | 99.93 | 84.86 | 9.62 | 4.14 | 0.95 | 0.35 | 99.92 |
| 29 wt % Ni doped bulk Cr | 100.00 | 81.37 | 11.69 | 4.17 | 1.84 | 0.72 | 99.78 |
| 10 wt % Ni doped bulk Cr | 94.74 | 89.11 | 6.70 | 1.10 | 1.93 | 1.04 | 99.88 |

As is evident from Table 2, the chromium oxyfluoride catalyst, which was obtained from Cr$_2$O$_3$ activated with HF, exhibited good conversion and selectivity for 1234yf.

Working Example 6—Dehydrofluorination of 245cb to 1234yf

The equipment described above in Example 5 was used to dehydrofluorinate 245cb to 1234yf, using the following conditions: 22 ml of a Cr/Ni/AlF$_3$ catalyst precursor was calcined at a temperature of 377° C. under atmospheric pressure. Using the chromium oxyfluoride catalyst thereby obtained, the conversion was 91% and the selectivity of the desired product, 1234yf, was 90%, as shown in FIG. 1.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A method for producing 2,3,3,3-tetrafluoropropene (HFO-1234yf) comprising dehydrofluorinating a pentafluoroalkane selected from the group consisting of 1,1,1,2,2-pentafluoropropane (HFC-245cb), 1,1,1,2,3-pentafluoropropane (HFC-245eb), and mixtures thereof in a gas phase in the presence of air and/or oxygen and a calcined chromium oxyfluoride catalyst, containing 1-20 weight % of a co-catalyst selected from the group consisting of Zn, Co, Mn, and Mg, wherein said catalyst is support or unsupported and wherein said catalyst is not activated with hydrogen fluoride and wherein said 2,3,3,3-tetrafluoropropene (HFO-1234yf) is produced directly from said pentafluoroalkane in a single step.

2. A method according to claim 1, wherein the catalyst comprises a support selected from the group consisting of alumina, graphite, chromia, zirconia, titania, magnesia, activated carbon, their corresponding HF-activated compounds, and mixtures thereof.

3. A method according to claim 1, wherein the calcined chromium oxyfluoride catalyst is formed by calcining CrF$_3$.xH$_2$O, where x is 1-10, in the presence of a flowing gas comprising nitrogen or air to form a calcined chromium oxyfluoride.

4. A method according to claim 1, wherein the catalyst is formed by calcining chromium (III) fluoride tetrahydrate.

5. A method according to claim 1, wherein the dehydrofluorination occurs at a temperature between about 200-800° C.

6. A method according to claim 1, wherein the calcined chromium oxyfluoride catalyst and the pentafluoroalkane are contacted for a time of about 10-200 seconds.

7. A method according to claim 1, wherein air and/or oxygen are co-fed with the pentafluoroalkane.

8. A method according to claim 1, wherein oxygen is present in the gas phase-in an amount effective to provide an oxygen to pentafluoroalkane molar ratio of about 0.1-10%.

9. A method for producing 2,3,3,3-tetrafluoropropene (HFO-1234yf) comprising:
   (a) forming a catalyst comprising calcined chromium oxyfluoride containing 1-20 weight % a co-catalyst selected from the group consisting of Zn, Co, Mn, and Mg, wherein said catalyst is not activated with hydrogen fluoride; and
   (b) dehydrofluorinating 1,1,1,2,2-pentafluoropropane (HFC-245cb), in a gas phase in the presence of air and/or oxygen and said calcined chromium oxyfluoride catalyst to form, directly, in a single step, 2,3,3,3-tetrafluoropropene (HFO-1234yf).

10. A method according to claim 9, wherein the catalyst is formed by calcining CrF3.xH2O, where x is 1-10, to form said calcined chromium oxyfluoride.

11. A method according to claim 10, wherein the calcination occurs in the presence of a flowing gas comprising nitrogen.

12. A method according to claim 10, wherein the calcination occurs at a temperature between about 200-1000° C.

13. A method according to claim 10, wherein a contact time during the calcination is about 10-100 seconds.

14. A method according to claim 9, wherein said calcined chromium oxyfluoride catalyst is pelletized.

* * * * *